(12) United States Patent
Marth et al.

(10) Patent No.: US 8,187,591 B2
(45) Date of Patent: May 29, 2012

(54) METHODS OF TREATING COAGULOPATHY

(75) Inventors: Jamey D. Marth, Goleta, CA (US);
Prabhjit Kaur Grewal, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/681,884

(22) PCT Filed: Oct. 10, 2008

(86) PCT No.: PCT/US2008/079615
§ 371 (c)(1),
(2), (4) Date: May 18, 2010

(87) PCT Pub. No.: WO2009/049234
PCT Pub. Date: Apr. 16, 2009

(65) Prior Publication Data
US 2010/0285028 A1 Nov. 11, 2010

Related U.S. Application Data

(60) Provisional application No. 60/979,366, filed on Oct. 11, 2007.

(51) Int. Cl.
*A61K 38/47* (2006.01)
*A61K 38/17* (2006.01)
*C12N 9/24* (2006.01)

(52) U.S. Cl. .................. 424/94.61; 424/158.1; 435/200
(58) Field of Classification Search .............. 424/94.61, 424/158.1; 435/200
See application file for complete search history.

(56) References Cited

U.S. PATENT DOCUMENTS

| | | | |
|---|---|---|---|
| 7,192,914 | B1 | 3/2007 | Marth et al. |
| 2002/0146411 | A1 | 10/2002 | Blackburn et al. |
| 2004/0087486 | A1 | 5/2004 | Hanson |
| 2005/0004020 | A1 | 1/2005 | Yu et al. |

FOREIGN PATENT DOCUMENTS

WO WO 0122921 A2 * 4/2001

OTHER PUBLICATIONS

TheFreeDictionary, definition for coagulopathy, http://medical-dictionary.thefreedictionary.com/coagulopathy, printed from the Internet on Sep. 8, 2011.*
Ellies, L., et al., "Sialyltransferase ST3Gal-IV operates as a dominant modifier of hemostasis by concealing asialoglycoprotein receptor ligands," *PNAS*, vol. 99(15), pp. 100042-100047 (Jul. 23, 2002).

* cited by examiner

*Primary Examiner* — Rosanne Kosson
(74) *Attorney, Agent, or Firm* — Kilpatrick Townsend & Stockton LLP

(57) ABSTRACT

The invention provides compositions and methods for enhancing clearance of coagulation factors {e.g., VWF) and platelets from the blood stream of a patient in need thereof. The methods comprise administering to the patient a therapeutically effective amount of an agent that increases clearance of coagulation factors or platelets. Such an agent can be, for example, a neuraminidase.

14 Claims, 8 Drawing Sheets

A

B

METHODS OF TREATING COAGULOPATHY

CROSS-REFERENCE TO RELATED APPLICATIONS

This application is a U.S. National Stage Application of PCT/US2008/079615, filed Oct. 10, 2008, which claims priority to U.S. Provisional Application No. 60/979,366, filed Oct. 11, 2007, the contents of which are herein incorporated by reference.

STATEMENT AS TO RIGHTS TO INVENTIONS MADE UNDER FEDERALLY SPONSORED RESEARCH AND DEVELOPMENT

This invention was made with government support under Grant No. HL57345, awarded by the National Institutes of Health. The United States Government has certain rights in the invention.

FIELD OF THE INVENTION

This invention relates to methods of treating of coagulopathy, in particular disseminated intravascular coagulation (DIC), resulting from a number of causes, including trauma, complications in pregnancy, cancer and the like.

BACKGROUND OF THE INVENTION

The Ashwell receptor is the major lectin of hepatocytes and rapidly clears from blood circulation glycoproteins bearing glycan ligands that include galactose and N-acetylgalactosamine. This asialoglycoprotein receptor activity remains a significant factor in the preparation and delivery of pharmaceuticals, yet a biological purpose of the Ashwell receptor has remained elusive. The ligands of the Ashwell receptor are endogenous glycoproteins and regulatory components in blood coagulation and thrombosis that include von Willebrand factor and platelets.

The liver controls the removal of exogenously administered glycoproteins from circulation as discovered by Ashwell and colleagues over 35 years ago (van den Hamer, C. J. A. et al., *J. Biol. Chem.*, 245:4397-4402 (1970); Morell, A. G. et al., *J. Biol. Chem.*, 246:1461-1467 (1971); Ashwell, G. and Morell, A., *Adv. Enzymol. Rel. Areas Mol. Biol.*, 41:99-128 (1974); Hudgin, R. L. et al., *J. Biol. Chem.*, 249:5536-5543 (1974)). These classical investigations identified the first vertebrate lectin as a hepatic receptor for glycoproteins bearing glycan chains that lack sialic acid, termed asialoglycoproteins (Ashwell, G. and Kawasaki, T., *Methods Enzymol.*, 50:287-288 (1978); Ashwell, G. and Harford, J., *Ann. Rev. Biochem.*, 51:531-534 (1982)).

The hepatic Ashwell receptor is one of multiple asialoglycoprotein receptors (ASGPRs) of the C-type lectin family and remains a fundamental consideration in design of clinical treatments to provide therapeutic levels of glycoproteins in circulation (Stockert, R. J., *Physiol. Rev.*, 75:591-609 (1995); Weis, W. I. et al., *Immunol. Rev.*, 163:19-34 (1998); Drickamer, K., *Curr. Opin. Struct. Biol.*, 9:585-590 (1999)). ASGPRs of mammals mediate the capture and endocytosis of a wide range of exogenously administered glycoproteins with galactose (Gal) or N-acetylgalactosamine (GalNAc) residues at the termini of their glycan chains. More recent findings have indicated that some sialylated glycans are also ligands for the Ashwell receptor (Park, E. I. et al., *Proc. Natl. Acad. Sci. USA*, 102:17125-17129 (2005)). Localized to the vascular face of the hepatocyte cell surface, ASGPRs are positioned to remove and degrade potentially deleterious circulating glycoproteins (Ashwell, G. and Harford, J., *Ann. Rev. Biochem.*, 51:531-534 (1982); Weigel, P. H., *Bioessays*, 16:519-524 (1994); Wahrenbrock, M. G. and Varki, A., *Cancer Res.*, 66:2433-2441 (2006)). Nevertheless, the biological purpose of ASGPR activity has remained mysterious. Endogenous ligands have been difficult to identify and conservation of the Ashwell receptor throughout vertebrate evolution remains unexplained.

The Ashwell receptor is composed of type-2 transmembrane glycoproteins termed Asgr-1 and Asgr-2 that are encoded by distinct but closely linked genes, with variation in Asgr-2 structure due to RNA splicing (Drickamer, K. et al., *J. Biol. Chem.*, 259:770-778 (1984); Halberg, D. F. et al., *J. Biol. Chem.*, 262:9828-9838 (1987); Paietta, E. et al., *J. Biol. Chem.*, 267:11078-11084 (1992)). Both Asgr-1 and Asgr-2 are highly conserved among mammalian species and may have originated from a single ancestral gene (Spiess, M. and Lodish, H. F., *Proc. Natl. Acad. Sci. USA*, 82:6465-6469 (1985); Hong, W. et al., *Hepatology*, 8:553-558 (1988); Takezawa, R. et al., *Biochim. Biophys. Acta*, 1171:220-222 (1993)). Although detectable in some extrahepatic tissues, the liver is the predominant site of their expression. Oligomerization of Asgr-1 and Asgr-2 has been observed in various cellular contexts with findings together supporting the possibility that Ashwell receptors may exist as Asgr-1/Asgr-2 hetero-oligomers, Asgr-1 trimers, and Asgr-2 dimers and tetramers, perhaps thereby altering substrate selectivity, binding affinities, and rates of endocytosis (Hardy, M. R. et al., *Biochemistry*, 24:22-28 (1985); Braiterman L. T. et al., *J. Biol. Chem.*, 264:1682-1688 (1989); Henis, Y. I. et al., *J. Cell Biol.*, 111:1409-1418 (1990); Bider, M. D. et al., *J. Biol. Chem.*, 271:31996-32001 (1996); Ruiz, N. I. and Drickamer, K., *Glycobiology*, 6:551-559 (1996); Saxena, A. et al., *J. Biol. Chem.*, 277:35297-35304 (2002); Weigel, P. H. et al., *Biochim. Biophys. Acta.*, 1572:341-363 (2002); Yik, J. H. N. et al., *J. Biol. Chem.*, 277:23076-23083 (2002)). Remarkably, while mice bearing reported null mutations in either Asgr-1 or Asgr-2 manifest decreased clearance of exogenous de-sialylated glycoproteins, they do not accumulate endogenous asialoglycoproteins in circulation, and lack significant intrinsic abnormalities (Ishibashi, S. et al., *J. Biol. Chem.*, 269:27803-27806 (1994); Braun, J. R. et al., *J. Biol. Chem.*, 271:21160 (1996); Tozawa R.-I. et al., *J. Biol. Chem.*, 276:12624-12628 (2001)).

A genetic approach to disrupt the expression of sialyltransferases among intact animals has revealed endogenous glycoprotein ligands for one or more ASGPRs (Ellies L. G. et al., *Proc. Natl. Acad. Sci. USA*, 99:10042-10047 (2002)). Specifically, when ST3Gal-IV sialyltransferase activity is limiting or absent, ASGPR ligands are unmasked on a subset of regulatory and pro-thrombotic components of the mammalian blood coagulation system, including Von Willebrand Factor (VWF) and platelets. Mice lacking ST3Gal-IV show prolonged bleeding and coagulation times (Ellies L. G. et al., *Proc. Natl. Acad. Sci. USA*, 99:10042-10047 (2002)).

Disseminated intravascular coagulation (DIC) is a life-threatening coagulopathy involving the consumption of coagulation factors and platelets with the deposition of intravascular fibrin throughout the body resulting in multi-organ failure (World Health Organization, *The Weekly Epidemiological Record*, 14:110 (2003); Remick, D. G., *Am. J. Pathol.*, 170:1435-1444 (2007)). As the small clots consume all the available coagulation factors and platelets, normal coagulation is disrupted and abnormal bleeding occurs. The small clots also disrupt normal blood flow to organs, which can result in organ failure and death.

Under normal hemostasis, the body maintains a balance between coagulation and fibrinolysis. The coagulation cascade yields thrombin that converts fibrinogen to fibrin, which forms a stable fibrin clot. The fibrinolytic system, which is activated in part by thrombin, then functions to break down the fibrin clot. Activation of the fibrinolytic system generates plasmin, which is responsible for the lysis of fibrin clots. In hemostasis, thrombin is the central proteolytic enzyme of coagulation and is also necessary for fibrinolysis.

In DIC, control of the processes of coagulation and fibrinolysis is lost, resulting in both widespread clotting and bleeding. DIC can be mediated by tissue factor (TF), which is released in response to exposure to cytokines and bacterial endotoxins. Upon activation, TF binds with coagulation factors that then trigger coagulation and an increase in circulating thrombin. At the same time, excess circulating thrombin leads to conversion of plasminogen to plasmin, resulting in fibrinolysis. The breakdown of clots results in excess amounts of fibrin degradation products (FDPs), which have powerful anticoagulant properties. Continued fibrin formation and fibrinolysis lead to hemorrhage from the consumption of coagulation factors and platelets and the anticoagulant effects of the FDPs.

DIC results from a number of clinical conditions, generally involving activation of systemic inflammation. Examples include, bacterial sepsis, viral infections, metastatic malignancies, and massive trauma.

The thrombohemorrhagic pathology associated with DIC continues to kill up to 50% of patients with severe septicemia in intensive care. In view of its life threatening nature, new methods for treating DIC are needed. This invention addresses these and other needs.

BRIEF SUMMARY OF THE INVENTION

This invention provides compositions and methods for enhancing clearance of coagulation factors (e.g., VWF) and platelets from the blood stream of a patient in need thereof. The methods comprise administering to the patient a therapeutically effective amount of an agent that increases clearance of coagulation factors or platelets. Such an agent can be, for example, a neuraminidase that expose the ligand recognized by hepatic asialoglycoprotein receptors (ASGPRs). The agent may also be an antibody that promotes clearance of coagulation factors and platelets. Such an antibody can be, for example, an antibody against an epitope present on a coagulation factor (e.g., VWF) or on the surface of a platelet. Examples of such anti-platelet antibodies include antibodies against CD41 and CD61. In particular, the methods are useful for treating DIC.

The neuraminidase may be administered as a polypeptide or as a nucleic acid that encodes the neuraminidase polypeptide.

The coagulopathy can be associated with a variety of diseases and conditions. Exemplary conditions include infections (e.g., bacterial sepsis, malaria, influenza), carcinomas, massive tissue injury, snake bite, heat stroke, and liver disease. Typically, the coagulopathy will be associated with infection by a pathogen, for example one having neuraminidase activity. In some cases the bacterium is *Streptococcus pneumoniae*.

The source of the neuraminidase polypeptide or nucleic acid is not critical. In some embodiments, the neuraminidase is a bacterial neuraminidase. Typical sources include human and bacterial (eg. *Arthrobacter ureafaciens* and *Vibrio cholerae*) sources. The polypeptides can be recombinantly produced, if desired.

The method of the invention may further comprise administering to the patient a sialyltransferase inhibitor. Typically, the sialyltransferase is ST3Gal IV. The method of sialyltransferase inhibitor may be an analog of a sialyltransferase substrate. The sialyltransferase inhibitor may be administered in conjunction with the neuraminidase or alone.

DEFINITIONS

The term "disseminated intravascular coagulation" ("DIC") refers to an acute or chronic thrombohemorrhagic disorder, which occurs in the course of a variety of clinical conditions. Examples include obstetric complications, infections (e.g., bacterial sepsis, malaria, influenza), carcinomas, massive tissue injury, snake bite, heat stroke, and liver disease.

The term "coagulation factor" refers to any of a number of proteins and other factors involved promoting blood coagulation. Examples include fibrinogen, prothrombin, thrombin, thrombokinase, VWF, and factors IV, V, VI, VII, VIII, IX, X, XI, XII, and XIII.

The term "antibody" as used herein is intended to include immunoglobulins and fragments thereof which are specifically reactive to the designated protein or peptide thereof. An antibody can include murine antibodies, human antibodies, primatized antibodies, chimeric antibodies, bispecific antibodies, humanized antibodies, antibodies fused to other proteins or radiolabels, and antibody fragments. Furthermore, an antibody herein is used in the broadest sense and specifically covers intact monoclonal antibodies, polyclonal antibodies, multispecific antibodies (e.g. bispecific antibodies) formed from at least two intact antibodies, and antibody fragments so long as they exhibit the desired biological activity. An "antibody" indicates all classes (e.g. IgA, IgD, IgE, IgG and IgM). Antibodies useful in the invention include antibodies against CD-41 or CD-61.

The term "neuraminidase" (sometimes referred to as a "sialidase") refers to a polypeptide that catalyzes the hydrolysis of α2-3, α2-6, and/or α2-8 linked N-acetyl-neuraminic acid (sialic acid) residues from a substrate, e.g., a glycoprotein, glycolipid or an oligosaccharide. The term also includes trans-sialidases (eg. from parasite, *Trypanosoma Cruzi*). In the present invention, the neuraminidase will typically expose an ASPGR ligand on a coagulation factor or a platelet (including Platelet Microparticles (MPs), which are membrane vesicles, shed by platelets, that carry antigens/glycoproteins similar to intact platelets. Platelet MPs can enhance activation of coagulation).

One of skill will recognize that the particular amino acid sequence of the neuraminidase polypeptide is not critical to the invention, so long the polypeptide has the desired activity. Thus the amino acid sequence may contain some variations such as amino acid deletion, addition, or substitution, as compared to a known neuraminidase. Typically, a neuraminidase polypeptide of the invention will maintain a substantial level sequence identity (e.g., at least 80%, 85%, 90%, 95%, or higher sequence homology) to previously identified neuraminidases, such as those exemplified here. The polypeptide may further contain additional amino acid sequence, which can be heterologous in origin (e.g., an epitope tag). In addition, a neuraminidase polypeptide need not be a full length neuraminidase, so long as the desired enzymatic activity is maintained.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

As used in herein, the terms "identical" or percent "identity," in the context of describing two or more polynucleotide or amino acid sequences (for example in reference to a neuraminidase polypeptides or nucleic acids exemplified here), refer to two or more sequences or subsequences that are the same or have a specified percentage of amino acid residues or nucleotides that are the same (i.e., a sequence has 80% identity, preferably 85%, 90%, 91%, 92%, 93, 94%, 95%, 96%, 97%, 98%, 99%, or 100% identity, to a reference sequence), when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 50 amino acids or nucleotides in length, or more preferably over a region that is 75-100 amino acids or nucleotides in length.

For sequence comparison, typically one sequence acts as a reference sequence (e.g., a neuraminidase polypeptide exemplified here), to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the website of the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

"Polypeptide," "peptide," and "protein" are used interchangeably herein to refer to a polymer of amino acid residues. All three terms apply to amino acid polymers in which one or more amino acid residue may be an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

The term "therapeutically effective amount," as used herein, refers to an amount that produces therapeutic effects for which a substance is administered. The effects include the prevention, correction, or inhibition of progression of the symptoms of a disease/condition and related complications to any detectable extent. In the present invention, the disease or condition will typically be a coagulopathy associated with sepsis such as DIC. The exact amount will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

DETAILED DESCRIPTION

Figure 1:
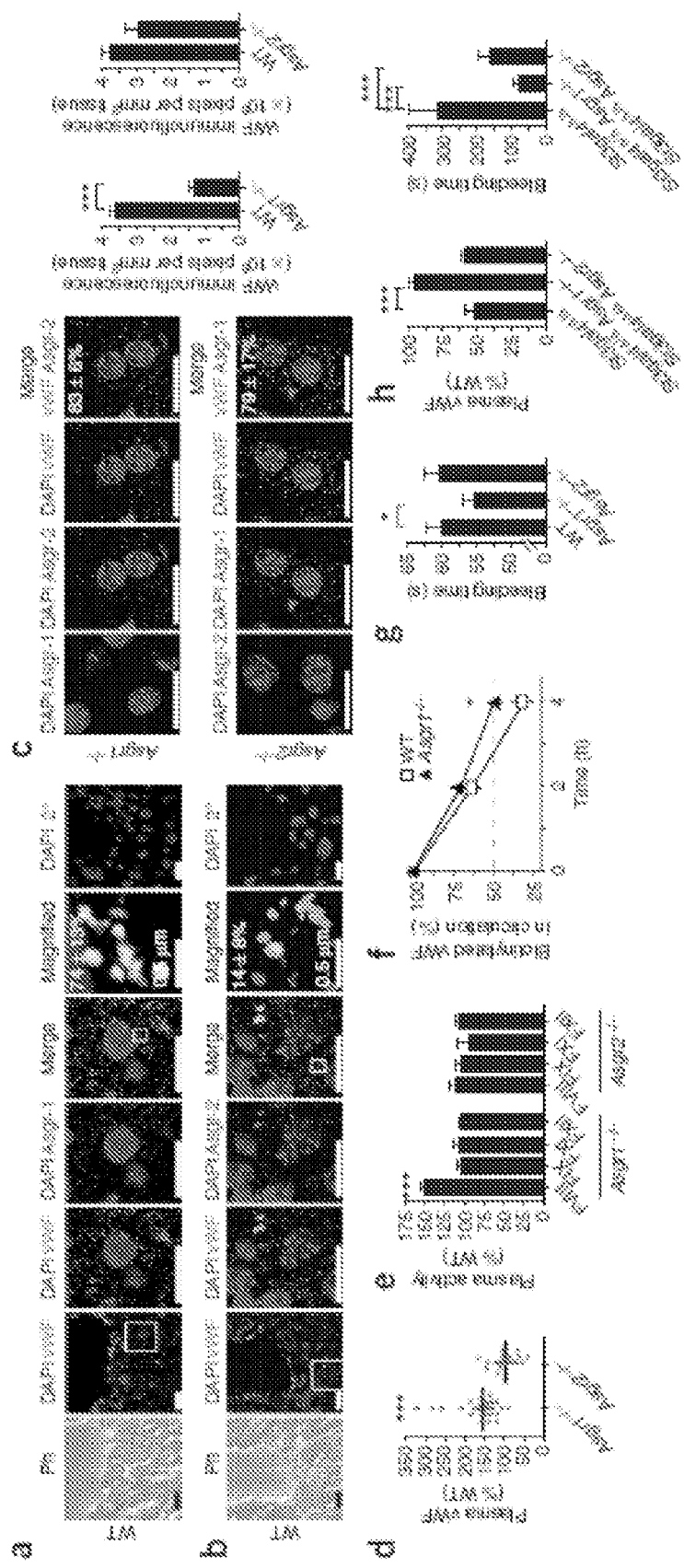
FIG. 1 Ashwell receptors of hepatocytes modulate vWF homeostasis and blood coagulation. (a-c) Liver sections from 8-week-old WT C57BL/6NHsd and Asgr-deficient mice imaged by phase-contrast (Ph) and fluorescent deconvolution microscopy using antibodies to vWF (green) and Asgpr-1 or Asgr-2 (red); DNA is stained by DAPI (blue). The percentage of vWF colocalized (yellow) with Asgr-1 (a) or Asgr-2 (b) in WT hepatocytes is indicated. Magnified views of the boxed regions are shown. Staining with Texas Red-conjugated secondary antibody to goat IgG (2°) alone is also shown. vWF abundance in Asgr-1-deficient hepatocytes compared to WT or Asgr-2-deficient hepatocytes is quantified (c). The percentage of vWF colocalized in Asgr-1-deficient or Asgr-2-deficient hepatocytes is indicated. The micrographs shown are representative of ten fields of view obtained from three mice of each genotype. All scale bars denote 5 µm unless otherwise indicated. (d) Plasma vWF abundance in mice lacking either Asgr-1 or Asgr-2. Horizontal bars indicate median vWF abundance, and vertical bars denote the interquartile range. (e) Coagulation factor measurements in mice lacking either Asgr-1 or Asgr-2 compared with WT littermates, *$P<0.001$. (f) Half-life of biotinylated plasma vWF from WT mice transfused into either WT or Asgr-1-deficient recipients. Plots represent data from eight WT and nine Asgr-1-deficient recipients. (g, h) Bleeding times (g) and bleeding times and plasma vWF abundance (h) in mice of the indicated genotypes. Mice homozygous for a null (deletion) mutation in the St3gal4 gene are denoted as St3gal4$^{\Delta/\Delta}$. Histograms include data from 20-25 mice of each genotype. All values are means±s.e.m.; *$P<0.001$; *$P<0.05$.

This invention provides methods of treating coagulopathies such as DIC. The methods of the invention are based, at least in part, on the discovery of an adaptive mechanism by which the body removes coagulation factors and platelets during sepsis. The marked thrombocytopenia that is closely associated with sepsis is not due to platelet consumption in thrombosis, as is generally thought in the prior art. Instead, reduced platelet abundance in circulation during the early phase of severe sepsis is due to Ashwell receptor-dependent platelet clearance in an adaptive response to retard the onset of lethal coagulopathy.

As demonstrated here, Ashwell receptors normally modulate VWF homeostasis and are poised to rapidly induce the thrombocytopenia associated with bacterial sepsis by eliminating platelets that have been de-sialylated by the bacterial or viral pathogens that have neuraminidase activity. Examples of pathogens which rely on neuraminidase activity for infection and/or replication include bacterial (eg. *Streptococcus pneumoniae/mitis, Hemophilus influenzae, Pseudomonas aeruginosa, Vibrio cholerae* and *Clostridium perfringens/sordelli. Salmonella typhi*), Viral (eg. influenza and para-influenza virus, mumps virus) and parasitic (eg. *Trypanosoma cruzi*). The methods of the invention are also useful for treating infections by pathogens that do not depend neuraminidase activity for infection (examples include Staphylococci and the Group A/Group B Streptococci).

Hemostatic adaptation by the Ashwell receptor moderates the onset and severity of DIC during sepsis and improves the probability of host survival. Moreover, administration of neuraminidase reduces circulating platelet levels by enhancing their clearance from blood. In particular, the methods of the invention provide a decreased time to death and survival advantage during severe sepsis.

Preparation of Neuraminidases or Genes Encoding them

Neuraminidase polypeptides used in the methods of the invention can be prepared according to well known recombinant production techniques. Basic texts disclosing general methods and techniques in the field of recombinant genetics include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994).

Polypeptides may also be synthesized by solid-phase peptide synthesis methods using well known procedures similar to those described by Merrifield et al., *J. Am. Chem. Soc.*, 85:2149-2156 (1963); Barany and Merrifield, *Solid-Phase Peptide Synthesis, in The Peptides: Analysis, Synthesis, Biology* Gross and Meienhofer (eds.), Academic Press, N.Y., vol. 2, pp. 3-284 (1980); and Stewart et al., *Solid Phase Peptide Synthesis* 2nd ed., Pierce Chem. Co., Rockford, Ill. (1984).

Preparation of Nucleic Acids Encoding Neuraminidases

Nucleic acids suitable for expressing the desired polypeptide can be cloned or obtained from a variety of sources. Neuraminidase genes can be cloned from a variety of organisms including mammals (e.g., humans), bacteria, and viruses. Exemplary human neuraminidases include Neu1 (GenBank Accession AF040958), Neu2 (GenBank Accession NM_005383), Neu3 (GenBank Accession NM_006656) and Neu4 (GenBank Accession NM_080741). Non-human sources include bacteria, such as *Arthrobacter ureafaciens* or *Vibrio Cholerae*.

The rapid progress in the studies of human genome has made possible a cloning approach where a human DNA sequence database can be searched for any gene segment that has a certain percentage of sequence homology to a known nucleotide sequence, such as one encoding a previously identified neuraminidase. Any DNA sequence so identified can be subsequently obtained by chemical synthesis and/or a polymerase chain reaction (PCR) technique such as overlap extension method. For a short sequence, completely de novo synthesis may be sufficient; whereas further isolation of full length coding sequence from a human cDNA or genomic library using a synthetic probe may be necessary to obtain a larger gene.

Alternatively, a nucleic acid sequence encoding a human neuraminidase can be isolated from a human cDNA or genomic DNA library using standard cloning techniques such as polymerase chain reaction (PCR), where homology-based primers can often be derived from a known nucleic acid sequence encoding a neuraminidase polypeptide. Most commonly used techniques for this purpose are described in standard texts, e.g., Sambrook and Russell, supra.

cDNA libraries suitable for obtaining a coding sequence for a neuraminidase from a variety of organisms are commercially available or can be constructed. The general methods of isolating mRNA, making cDNA by reverse transcription, ligating cDNA into a recombinant vector, transfecting into a recombinant host for propagation, screening, and cloning are well known (see, e.g., Gubler and Hoffman, Gene, 25: 263-269 (1983); Ausubel et al., supra). Upon obtaining an amplified segment of nucleotide sequence by PCR, the segment can be further used as a probe to isolate the full length polynucleotide sequence encoding the fibrinogen γ chain from the cDNA library. A general description of appropriate procedures can be found in Sambrook and Russell, supra.

A similar procedure can be followed to obtain a full-length sequence encoding a human neuraminidase, e.g., any one of the GenBank Accession Nos. mentioned above, from a human genomic library. Human genomic libraries are commercially available or can be constructed according to various art-recognized methods.

Based on sequence homology, degenerate oligonucleotides can be designed as primer sets and PCR can be performed under suitable conditions (see, e.g., White et al., PCR Protocols: Current Methods and Applications, 1993; Griffin and Griffin, PCR Technology, CRC Press Inc. 1994) to amplify a segment of nucleotide sequence from a cDNA or genomic library. Using the amplified segment as a probe, the full-length nucleic acid encoding a neuraminidase is obtained.

The amino acid sequence of a neuraminidase polypeptide may be modified while maintaining or enhancing the polypeptide's capability to hydrolyze sialic acid residues, as determined by standard in vitro methods to measure neuraminidase activity. Such assays typically include a sialic acid containing substrate, a means for detecting sialic acid cleaved from the substrate and assay conditions suitable for neuraminidase activity. Such assays are well known to those of skill in the art.

Possible modifications to the amino acid sequence may include conservative substitutions; deletion or addition of one or more amino acid residues (e.g., addition at one terminal of the polypeptide of a tag sequence such as 6×His to facilitate purification or identification); truncation of transmembrane domains and the like.

A variety of mutation-generating protocols are established and described in the art, and can be readily used to modify a polynucleotide sequence encoding a neuraminidase polypeptide. The procedures can be used separately or in combination to produce variants of a set of nucleic acids, and hence variants of encoded polypeptides. Kits for mutagenesis, library construction, and other diversity-generating methods are well known and commercially available.

The polynucleotide sequence can be further altered to coincide with the preferred codon usage of a particular host. For example, the preferred codon usage of one strain of bacterial cells can be used to derive a polynucleotide that encodes a neuraminidase polypeptide of the invention and includes the codons favored by this strain according to methods well known in the art.

Following preparation of the coding sequence, the neuraminidase polypeptide of the present invention can be produced using routine techniques in the field of recombinant genetics, relying on the polynucleotide sequences encoding the polypeptide disclosed herein.

Expression Systems

To obtain high level expression of a nucleic acid encoding a neuraminidase polypeptide of the present invention, one typically subclones a polynucleotide encoding the polypeptide into an expression vector that contains a strong promoter to direct transcription, a transcription/translation terminator and a ribosome binding site for translational initiation. Suitable bacterial promoters are well known in the art and described, e.g., in Sambrook and Russell, supra, and Ausubel et al., supra. Bacterial expression systems for expressing the neuraminidase polypeptide are available in, e.g., E. coli, Bacillus sp., and Salmonella. Kits for such expression systems are commercially available. Eukaryotic expression systems for mammalian cells, yeast, fungi, plants, and insect cells are well known in the art and are also commercially available.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically includes a transcription unit or expression cassette that contains all the additional elements required for the expression of the neuraminidase polypeptide in host cells. A typical expression cassette thus contains a promoter operably linked to the nucleic acid sequence encoding the polypeptide and signals required for efficient polyadenylation of the transcript, ribosome binding sites, and translation termination. The nucleic acid sequence encoding the polypeptide is typically linked to a cleavable signal peptide sequence to promote secretion of the polypeptide by the transformed cell. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as a baculovirus vector in insect cells, with a polynucleotide sequence encoding the polypeptide under the direction of the polyhedrin promoter or other strong baculovirus promoters.

The elements that are typically included in expression vectors also include a replicon that functions in E. coli, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary. Similar to antibiotic resistance selection markers, metabolic selection markers based on known metabolic pathways may also be used as a means for selecting transformed host cells.

Standard transfection methods are used to produce bacterial, mammalian, yeast, insect, or plant cell lines that express large quantities of a neuraminidase polypeptide, which is then purified using standard techniques (see, e.g., Colley et al., *J. Biol. Chem.* 264: 17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132: 349-351 (1977); Clark-Curtiss & Curtiss, *Methods in Enzymology* 101: 347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA, or other foreign genetic material into a host cell (see, e.g., Sambrook and Russell, supra). It is only necessary that the particular genetic engineering procedure used be capable of successfully introducing at least one gene into the host cell capable of expressing the polypeptide.

After the expression vector is introduced into appropriate host cells, the transfected cells are cultured under conditions favoring expression of the neuraminidase polypeptide. The cells are then screened for the expression of the recombinant polypeptide, which is subsequently recovered from the culture using standard techniques (see, e.g., Scopes, *Protein Purification: Principles and Practice* (1982); U.S. Pat. No. 4,673,641; Ausubel et al., supra; and Sambrook and Russell, supra).

Increasing the Half-Life of Administered Neuraminidase

In some embodiments, it may be useful to increase the bioavailability of the administered neuraminidase polypeptides. Increased serum half life of the polypeptides of the invention may be achieved through the use of polymers to conjugate, complex with, or absorb the neuraminidase. The increased half-life may be achieved by conjugating the polypeptide with appropriate macromolecules (for example, serum immunoglobulins, polysaccharides, polyesters, polyamino acids, homopolymers polyvinyl pyrrolidone, ethylenevinylacetate, methyl-cellulose, or carboxymethylcellulose, and acrylamides such as N-(2-hydroxypropyl) methacrylamide).

For example, the neuraminidase can be bound to molecules of inert polymers known in the art, such as a molecule of polyethylene glycol (PEG). Pegylation can extend the in vivo presence and thus therapeutic effectiveness of the neuraminidase polypeptides. Pegylation also reduces the potential antigenicity of the administered neuraminidase. Pegylation can also enhance the solubility of the administered neuraminidase thereby improving their therapeutic effect. Neuraminidase polypeptides can be pegylated according to well know techniques, for example as shown in Harris et al., "Pegylation, A Novel Process for Modifying Pharmacokinetics", Clin. Pharmacokinet, 2001:40(7); 539-551.

This approach has been applied clinically, allowing bacterial enzymes such as L-asparaginase to be administered repeatedly (Abuchowski, A. et al., Cancer Biochem. Biophys., 7: 175-186, 1984; Ettinger, L. J. et al., Cancer, 75: 1176-1181, 1995). Pegylation of enzymes and smaller proteins such as interleukin-2 has led to enhanced serum half-life, resulting in smaller doses and longer administration intervals without loss of clinical effectiveness (Teppler, H. et al., J. Exp. Med., 177: 483-492, 1993).

One of skill will recognize that the particular PEG moeity used can vary widely. Other polyalkylene glycol compounds, such as polypropylene glycol, may also be used. Other appropriate polymer conjugates include, but are not limited to, non-polypeptide polymers, charged or neutral polymers of the following types: dextran, colominic acids or other carbohydrate based polymers, biotin deriviatives and den-drimers, for example.

The PEG can be linked to an N-terminal amino acid of the neuraminidase, and/or can be linked to an amino acid residue downstream of the N-terminal amino acid, such as lysine, histidine, tryptophan, aspartic acid, glutamic acid, and cysteine. Cysteine-pegylated polypeptides, for example, can be created by attaching polyethylene glycol to a thio group on a cysteine residue of the neuraminidase molecule.

The PEG moiety attached to the protein may range in molecular weight from about 200 to 20,000 MW. The actual number of PEG moieties covalently bound per neuraminidase polypeptide may vary widely depending upon a number of factors, including the desired neuraminidase stability (i.e. serum half-life), activity, and the like.

Techniques for linking PEG molecules to polypeptides are well known and are described, for example, in U.S. Pat. Nos. 4,179,337; 5,382,657; 5,972,885; 6,177,087; 6,165,509; 5,766,897; and 6,217,869.

Administration of Antibodies, Neuraminidases or Genes Encoding them

The present invention also provides pharmaceutical compositions comprising an effective amount of an antibody of the invention, a neuraminidase polypeptide or a polynucleotide encoding the polypeptide. Pharmaceutical compositions of the invention are suitable for use in a variety of drug delivery systems. Suitable formulations for use in the present invention are found in *Remington's Pharmaceutical Sciences*, Mack Publishing Company, Philadelphia, Pa., 17th ed. (1985). For a brief review of methods for drug delivery, see, Langer, *Science* 249: 1527-1533 (1990).

The pharmaceutical compositions of the present invention can be administered by various routes, e.g., oral, subcutaneous, transdermal, intramuscular, intravenous, or intraperitoneal. The preferred routes of administering the pharmaceutical compositions are intravenous systemic delivery doses of about 500 U to about 3000 U, preferably 1000 U, of a neuraminidase activity for a 70 kg adult human. The appropriate dose may be administered in a single dose or as multiple doses presented at appropriate intervals, for example over the course of two, three, four, or more days. As used herein, one unit of neuraminidase activity defined as the amount of enzyme that will liberate 1 µmole of N-acetylneuraminic acid per minute at 37° C.

For preparing pharmaceutical compositions containing an antibody or a neuraminidase polypeptide, inert and pharmaceutically acceptable carriers are used. The pharmaceutical carrier can be either solid or liquid. Solid form preparations include, for example, powders, tablets, dispersible granules, capsules, cachets, and suppositories. A solid carrier can be one or more substances that can also act as diluents, flavoring agents, solubilizers, lubricants, suspending agents, binders, or tablet disintegrating agents; it can also be an encapsulating material.

In powders, the carrier is generally a finely divided solid that is in a mixture with the finely divided active component, e.g., a neuraminidase polypeptide. In tablets, the active ingredient is mixed with the carrier having the necessary binding properties in suitable proportions and compacted in the shape and size desired.

For preparing pharmaceutical compositions in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient of neuraminidase polypeptide. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The pharmaceutical compositions can include the formulation of the active compound of a neuraminidase polypeptide with encapsulating material as a carrier providing a capsule in which the neuraminidase polypeptide (with or without other carriers) is surrounded by the carrier, such that the carrier is thus in association with the compound. In a similar manner, cachets can also be included. Tablets, powders, cachets, and capsules can be used as solid dosage forms suitable for oral administration.

Liquid pharmaceutical compositions include, for example, solutions suitable for oral or parenteral administration, suspensions, and emulsions suitable for oral administration. Sterile water solutions of the active component (e.g., a neuraminidase polypeptide) or sterile solutions of the active component in solvents comprising water, buffered water, saline, PBS, ethanol, or propylene glycol are examples of liquid compositions suitable for parenteral administration. The compositions may contain pharmaceutically acceptable auxiliary substances as required to approximate physiological conditions, such as pH adjusting and buffering agents, tonicity adjusting agents, wetting agents, detergents, and the like.

Sterile solutions can be prepared by dissolving the active component (e.g., a neuraminidase polypeptide) in the desired solvent system, and then passing the resulting solution through a membrane filter to sterilize it or, alternatively, by dissolving the sterile compound in a previously sterilized solvent under sterile conditions. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9, and most preferably from 7 to 8.

The pharmaceutical compositions containing neuraminidase polypeptides can be administered for prophylactic and/or therapeutic treatments. In therapeutic applications, compositions are administered to a patient already suffering from a coagulopathy, in an amount sufficient to prevent, cure, reverse, or at least partially slow or arrest the symptoms of the condition and its complications. An amount adequate to accomplish this is defined as a "therapeutically effective dose."

In prophylactic applications, pharmaceutical compositions containing neuraminidase polypeptides are administered to a patient susceptible to or otherwise at risk of developing a disease or condition in which coagulation is undesirable, in an amount sufficient to delay or prevent the onset of the symptoms. Such an amount is defined to be a "prophylactically effective dose."

Single or multiple administrations of the compositions can be carried out with dose levels and pattern being selected by the treating physician. In any event, the pharmaceutical formulations should provide a quantity of a neuraminidase polypeptide sufficient to effectively promote clearance of coagulation factors (e.g., VWF) and platelets in the patient, either therapeutically or prophylactically.

Therapeutic Applications Using Nucleic Acids

In addition to delivery of a neuraminidase polypeptide, the therapeutic methods of the invention can also be carried out by delivery of a polynucleotide encoding the neuraminidase polypeptide. Examples of vectors used for such purposes include expression plasmids capable of directing the expression of the nucleic acids in the target cell. In other instances, the vector is a viral vector system wherein the polynucleotide is incorporated into a viral genome that is capable of transfecting the target cell.

Viral vector systems useful in the expression of therapeutic polypeptides include, for example, naturally occurring or recombinant viral vector systems. Depending upon the particular application, suitable viral vectors include replication competent, replication deficient, and conditionally replicating viral vectors. For example, viral vectors can be derived from the genome of human or bovine adenoviruses, vaccinia virus, herpes virus, adeno-associated virus, and retroviruses (including but not limited to Rous sarcoma virus), and MoMLV. Typically, the genes of interest are inserted into such vectors to allow packaging of the gene construct, typically with accompanying viral DNA, followed by infection of a sensitive host cell and expression of the gene of interest.

As used herein, "gene delivery system" refers to any means for the delivery of a nucleic acid of the invention to a target cell. In some embodiments of the invention, nucleic acids are conjugated to a cell receptor ligand for facilitated uptake (e.g., invagination of coated pits and internalization of the endosome) through an appropriate linking moiety, such as a DNA linking moiety (Wu et al., *J. Biol. Chem.* 263:14621-14624 (1988); WO 92/06180).

Similarly, viral envelopes used for packaging gene constructs that include the nucleic acids of the invention can be modified by the addition of receptor ligands or antibodies specific for a receptor to permit receptor-mediated endocytosis into specific cells (see, e.g., WO 93/20221, WO 93/14188, and WO 94/06923). In some embodiments of the invention, the DNA constructs of the invention are linked to viral proteins, such as adenovirus particles, to facilitate endocytosis (Curiel et al., *Proc. Natl. Acad. Sci. U.S.A.* 88:8850-8854 (1991)). In other embodiments, molecular conjugates of the instant invention can include microtubule inhibitors (WO/

9406922), synthetic peptides mimicking influenza virus hemagglutinin (Plank et al., *J. Biol. Chem.* 269:12918-12924 (1994)), and nuclear localization signals such as SV40 T antigen (WO93/19768).

Reducing Biosynthesis of Oligosaccharides Having a Terminal Linked Sialic Acids

In addition to removing sialic acids using neuraminidases, the invention also provides methods for reducing biosynthesis of sialylated oligosaccharides. As noted above, when ST3Gal-IV sialyltransferase activity is limiting or absent, ASGPR ligands can be unmasked on VWF and platelets (see, Ellies L. G. et al., *Proc. Natl. Acad. Sci. USA,* 99:10042-10047 (2002)). Methods for inhibiting the activity of this enzyme are described for example in U.S. Pat. No. 7,192,914.

Thus, the invention also provides methods of enhancing clearance of coagulation factors (e.g., VWF) and platelets by preventing biosynthesis of oligosaccharides that terminate in sialic acids using inhibitors of sialyltransferases, such as ST3Gal IV. Typically, α 2,3 linked sialic acid moieties are targeted. As explained below, the expression of the sialyltransferase gene can be inhibited or the enzymatic activity of the protein can be inhibited.

Sialyltransferase Inhibitors

Several inhibitors of sialyltransferases are known in the art. For example, analogs of sialyltransferase substrates are suitable for use as inhibitors. Substrate analogs of both the donor (e.g., analogs of CMP-sialic acid) and the acceptor have been reported which serve as sialyltransferase inhibitors (Schaub et al. (1998) *Glycoconjugate J.* 15: 345-354; Schaub and Schmidt (1996) *Abstract C* 10, Second European Conference on Carbohydrate Mimics, La Garda (Italy); Amann et al. (1998) *Chem. Eur. J.* 4: 1106-1115; Müller et al. (1998) *Tetrahedron Lett.* 39: 509-512; Korytnyk et al. (1980) *Eur. J. Med. Chem.* 15: 77-84; Kijima-Suda et al. (1986) *Cancer Res.* 46: 858-862; Khan et al. (1992) In *Glycoconjugates, Composition, Structure, Function* (Eds.: H. J. Allen, E. C. Kisailus). M. Dekker, New York, pp. 361-378 and references therein; Hashimoto et al. (1993) *Carbohydr. Res.* 247: 179-193; Imamoto and Hashimoto (1996) *Tetrahedron Lett.* 37: 1451-1454; Kleineidam et al. (1997) *Glycoconjugate J.* 14: 57-66). Transition state analogs are also useful as sialyltransferase inhibitors.

Additional inhibitors of the sialyltransferase can be readily identified by screening methods known to those of skill in the art. Sialyltransferase activity and its inhibition is typically assayed according to standard methods for determining enzyme activity. For a general discussion of enzyme assays, see, Rossomando, "Measurement of Enzyme Activity" in *Guide to Protein Purification*, Vol. 182, Methods in Enzymology (Deutscher ed., 1990), and Fersht, *Enzyme Structure and Mechanism* (2d ed. 1985). Enzyme inhibition of kinetically complex systems involving more than one substrate, as is the case for glycosyltransferases, are described in Segel, *Enzyme Kinetics*, (Wiley, N.Y. 1975), which is incorporated herein by reference.

Inhibition of sialyltransferase (e.g., ST3Gal IV) activity can also be achieved through the use of inhibitory nucleic acids that inhibit sialyltransferase gene expression. Inhibitory nucleic acids can be single-stranded nucleic acids that comprise a sequence complementary to nucleic acids that encode sialyltransferases, such as ST3Gal IV. These nucleic acids can be, for example, siRNA molecules or antisense nucleic acids.

In one embodiment, the inhibitory nucleic acid can specifically bind to a target nucleic acid that encodes, for example, an ST3Gal IV sialyltransferase. The nucleotide sequence of a human ST3Gal IV cDNA is reported in Kitagawa and Paulson (1994) *J. Biol. Chem.* 269: 1394-401. This nucleotide can be used as a probe for the identification of ST3Gal IV-encoding nucleic acids from other species. From the human or other ST3Gal IV-encoding nucleotide sequences, one can derive suitable inhibitory nucleic acids. Administration of such inhibitory nucleic acids to a mammal can reduce circulating levels of sialylated platelets by reducing or eliminating the biosynthesis of Siaα2,3Gal-containing oligosaccharides.

Once sialyltransferase inhibitors are identified, they can be tested for the ability to retain the desialylated character of platelets upon administration to laboratory animals. Animals can be treated with pharmacological doses of the inhibitor to block addition of sialic acid to cell surface carbohydrates of platelets. The effect of the inhibitor on levels of desialylated platelets is then determined.

EXAMPLES

The following examples are offered to illustrate, but not to limit the claimed invention.

Example 1

This example shows that Ashwell receptors rapidly induce the thrombocytopenia associated with bacterial sepsis by eliminating platelets that have been de-sialylated by the bacterial NanA neuraminidase. Hemostatic adaptation by the Ashwell receptor moderates the onset and severity of DIC during sepsis and improves the probability of host survival.

Methods

Mice. Asgr1 mutant mice (Soukharev, S. et al., *Nucleic Acids Res.,* 27:e21 (1999)) were kindly provided by B. Sauer (Stowers Institute for Medical Research, Kansas City, Mo.). We purchased Asgr2 mutant mice from The Jackson Laboratory, stock 002387 (Ishibashi, S. et al., *J. Biol. Chem.,* 269: 27803-27806 (1994)). Mice bearing a mutation in the gene encoding ST3Gal-IV (St3gal4) have been previously described (Ellies, L. G. et al., *Proc. Natl. Acad. Sci. USA,* 99:10042-10047 (2002)). We generated mice homozygous for multiple mutant alleles from parental mice with St3gal4$^{\Delta/\Delta}$ Asgr1$^{+-}$ or St3gal4$^{\Delta/\Delta}$ Asgr2$^{+-}$ genotypes. We observed no phenotypic differences between males and females. Prior to experimentation, we backcrossed all strains of mice to C57BL/6NHsd mates for at least eight generations and provided sterile pellet food and water ad libitum. We used littermates aged 8-13 weeks in all studies presented. All animal use and procedures were approved by the Institutional Animal Care and Use Committee of the University of California, San Diego.

Histology. For histological staining, we used tissues fixed in 10% buffered formalin, trimmed, processed, embedded in paraffin and sectioned at a width of 5 μm. For immunofluorescence studies, we stained glass slides bearing 5-μm sections of frozen embedded liver tissue (in OCT medium; Sakura Finetek). Antibodies included FITC-conjugated sheep antibody to human vWF (Abeam), goat antibody to mouse ASGPR1 and goat antibody to human ASGPR2 (Santa Cruz Biotech), phycoerythrin (PE)-conjugated rat antibody to mouse CD41 (BD Pharmingen), Alexa Fluor 647-phalloidin to detect actin (Invitrogen), FITC-conjugated rat antibody to mouse CD68 (Serotec) and Texas Red-conjugated antibody to goat IgG secondary antibodies (Jackson ImmunoResearch Labs). We performed all primary antibody incubations (1:200) at 4° C. overnight and secondary antibody incubations (1:1,000) at 22° C. for 1 h and then mounted the slides with aqueous gel mount (Biomeda). We obtained images by fluorescence deconvolution microscopy with a DeltaVision Restoration microscope (Applied Precision) and analyzed them with DeltaVision SoftWorx (Version 2.50). We acquired and processed images identically within all comparative studies. Images were quantified for immunofluorescence signal, colocalization or both with MetaMorph software (Universal Imaging).

At 24-48 h after infection with *S. pneumoniae*, we collected organs for histopathological and morphometric examination. Organs from mice determined to have equivalent amounts of bacteria in the blood were immersion-fixed, embedded in paraffin, sectioned and stained with H&E (Surgipath) using standard histological techniques. We prepared the Fraser-Lendrum stain (Sigma) and used it to identify fibrin deposition (red) and red blood cells (yellow or orange). Two investigators blind to the experimental group microscopically examined the stained tissue sections for semiquantitative analysis. We scored 20 randomly selected fields of view for fibrin deposits in capillaries. We counted 100 central and portal veins from random liver sections at three tissue depths and scored them as unclotted owing to the presence of red blood cells, clotted owing to visible fibrin thrombi or empty owing to upstream thrombi. We scored 20 randomly selected fields of view for fibrin deposits in sinusoids and used 30 randomly selected fields of view to assess pyknotic bodies and hepatocyte necrosis.

Hematology. We anesthetized mice by a mixture of 3% isoflurane with oxygen in an induction chamber maintained with a nose cone outside of the induction chamber. We transected tails of mice with a sterile razor blade 2 mm from the tip, collected whole blood (100 µl) in EDTA-containing polypropylene microtubes (Becton Dickinson) to ensure proper anticoagulation and kept the tubes at 22° C. until we could analyze them (within 4 h). We acquired blood cell counts with leukocyte differentials and platelet counts in duplicate on a Hemavet 850FS Multi Species Hematology System (Drew Scientific) programmed with mouse hematology settings. We prepared a whole-blood smear from each sample and Wright stained it for manual viewing. We performed coagulation factor analyses and clotting time assays as previously described (Ellies, L. G. et al., *Proc. Natl. Acad. Sci. USA*, 99:10042-10047 (2002)).

von Willebrand factor analysis. We used vWF antibody and lectin binding assays to determine vWF glycosylation and glycoprotein abundance as previously described (Ellies, L. G. et al., *Proc. Natl. Acad. Sci. USA*, 99:10042-10047 (2002)). We determined vWF half-life after ex vivo biotinylation also as previously described (Ellies, L. G. et al., *Proc. Natl. Acad. Sci. USA*, 99:10042-10047 (2002)).

Figure 2:
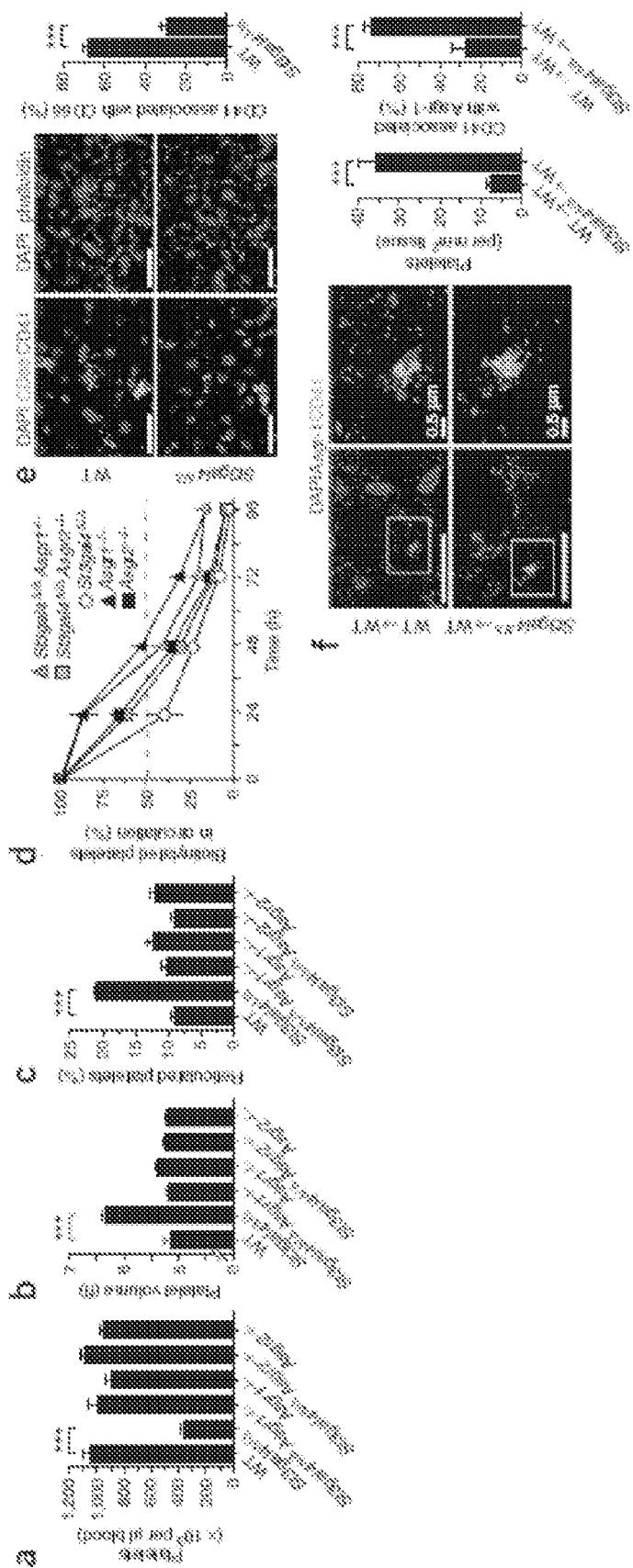
FIG. 2 The Ashwell receptor and the ST3Gal-IV sialyltransferase participate in platelet clearance. (a-c) Platelet abundance (a), mean platelet volume (b), and reticulated platelet frequencies (c) in mice of indicated genotypes. Histograms include data from 20-25 mice of each genotype. (d) Platelet half-life analyses in mice of indicated genotypes. Each curve includes data from six mice. Three separate experiments were performed. (e) Platelet antigens (CD41, left images) were detected in perfused liver sections of WT and St3gal4$^{\Delta/\Delta}$ mice, and hepatocytes were further visualized with DAPI and the actin-binding protein phalloidin (right images). Kupffer cells were detected by antibodies to CD68 (green). The images shown are representative of multiple fields of view from three mice of each genotype, comprising a total of 200 separate CD41 signals. (f) Sections of perfused liver were analyzed from WT recipients of biotinylated platelet-rich plasma from donors of the indicated genotypes to detect platelets (CD41, green) and Asgr-1 (red). Images are representative of multiple fields of view from three mice of each genotype, comprising a total of 46 separate CD41 signals. Scale bars denote 5 µm unless otherwise indicated. ***$P<0.001$. All values are means±s.e.m.
Figure 3:
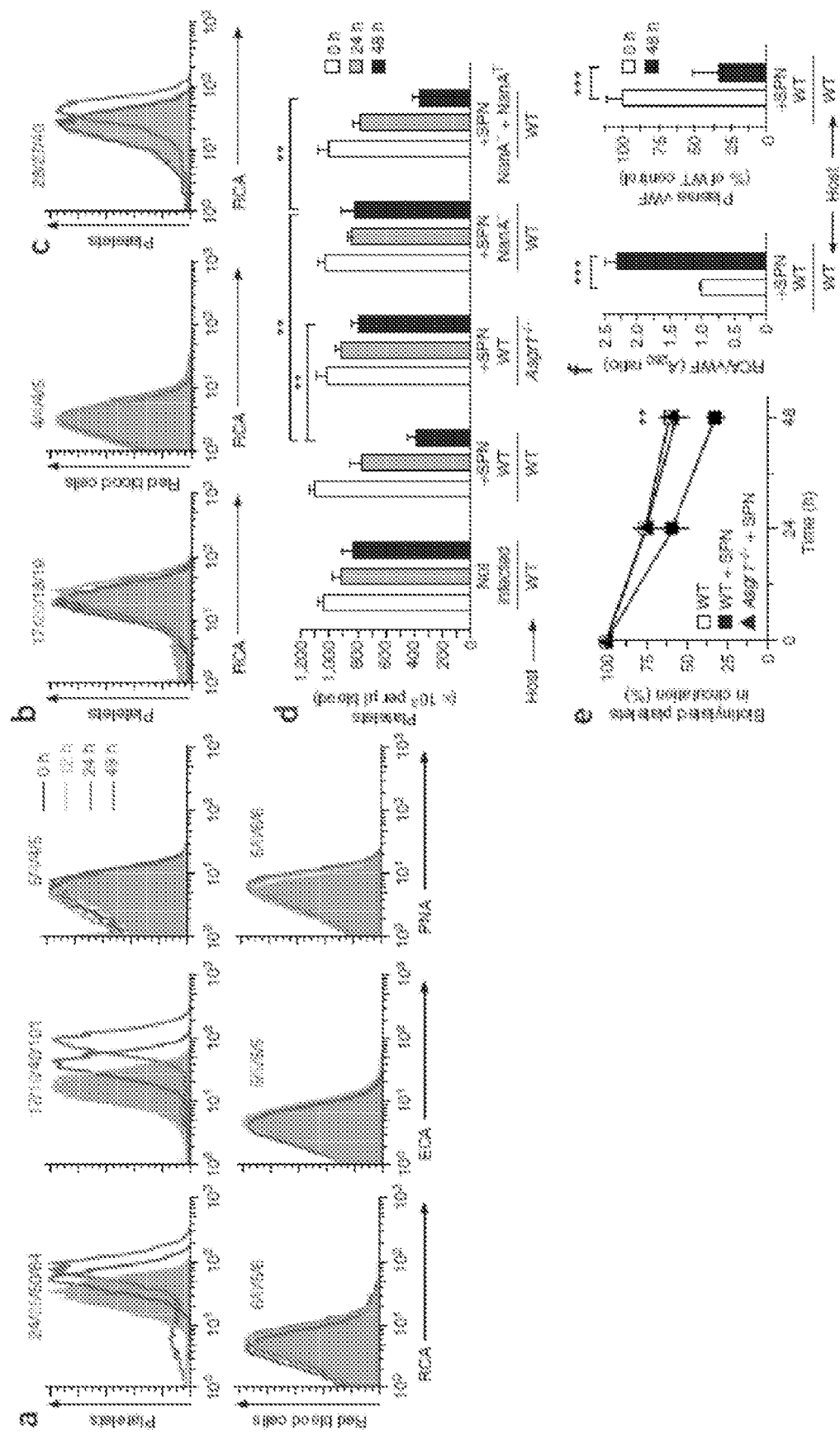
FIG. 3 Thrombocytopenia caused by NanA-dependent platelet desialylation and Ashwell receptor function in *S. pneumoniae* infection. (a) Asialoglycoproteins were detected by *Ricinus communis* agglutinin (RCA) and *Erythrina cristagalli* agglutinin (ECA) lectin binding at the indicated times after infection with *S. pneumoniae* strain D39 (*S. pneumoniae* WT). PNA lectin binding was used to detect the Thomsen Friedenrich antigen. Mean fluorescence is enumerated at the indicated times after infection. (b) Detection of asialoglycoproteins on platelets and red blood cells after infection with the *S. pneumoniae* NanA$^-$ mutant. Data in a and b are representative of three to five independent experiments comparing at least six mice per group. (c) Detection of asialoglycoproteins on platelets after infection with the *S. pneumoniae* NanA$^-$ mutant complemented by a functional nanA gene in trans (NanA$^T$). Data are representative of four mice analyzed. (d) Platelet abundance in four to eight mice of the indicated genotypes after infection with *S. pneumoniae* WT, *S. pneumoniae* NanA$^-$ or *S. pneumoniae* NanA$^-$ complemented with NanA$^T$ (NanA$^-$+NanA$^T$). Similar results were obtained after *S. pneumoniae* WT infection of Asgr-2-deficient mice (data not shown). SPN, *S. pneumoniae*. (e) Platelet turnover in uninfected WT mice and in WT or Asgr-1-deficient mice after *S. pneumoniae* WT infection. Each plot includes data from six mice. (f) Detection of asialo-vWF by RCA lectin binding and total vWF levels at 0 and 48 h after infection with *S. pneumoniae* WT when bacteremia was >1×10$^9$ CFU/ml. Each histogram presents data from four to six mice. All comparative analyses were performed on mice with equivalent levels of bacteremia at each timepoint. *$P<0.001$ and $P<0.01$. All values are means±s.e.m.

Platelet measurements. We collected whole blood from retro-orbital or tail bleeds into EDTA-Vacutainer tubes (Becton Dickinson) and diluted it 1:30 in Tyrode's buffer (150 mM NaCl, 5 mM KCl, 1 mM $MgSO_4$, 10 mM HEPES, pH 7.4) before staining for flow cytometric analyses to determine glycosylation status (Ellies, L. G. et al., *Proc. Natl. Acad. Sci. USA*, 99:10042-10047 (2002)), circulating platelet half-life or percentage of reticulated platelets. We performed all platelet analyses at 22° C. We determined platelet half-lives after in vivo biotinylation by infusion of N-hydroxysuccinimide-biotin (Pierce). We injected 10 mg of N-hydroxysuccinimide-biotin (dissolved in DMSO, diluted to 500 µl volume in PBS) per kg of mouse body weight into the lateral tail vein. We collected 30 µl of whole blood by tail bleed from anesthetized mice at 24-h intervals as indicated in FIGS. 2 and 3 for analysis by flow cytometry; time 0 measurements were determined 1 h after biotin injection. We determined the percentage of biotinylated cells by flow cytometric measurements of light scatter and detection by binding of PE-conjugated streptavidin and FITC-conjugated antibody to CD41 (platelets) and APC-conjugated antibody to ter199 (red blood cells) (BD Pharmingen). Biotinylation efficiency varied between 80-95%. Levels of biotinylated platelets and red blood cells in circulation were based on measurements at time 0, denoted as 100%.

We calculated the percentage of reticulated platelets using RNA staining methods with Thiazole Orange (TO; Sigma). We diluted 2 µl of whole blood 1:30 in Tyrode's buffer and incubated it with 0.1 µg of PE-conjugated CD41-specific antibody at a final concentration of 1 µg/ml TO in PBS (stock of 1 mg/ml dissolved in methanol) for 10 min in the dark at 22° C. We collected and analyzed flow cytometric data on 10,000 platelets. We confirmed identification of TO-positive platelets with RNase-pretreated whole blood.

*Streptococcus pneumoniae* infection. Wild-type *S. pneumoniae* serotype 2 strain D39 and its isogenic NanA$^-$ mutant[35] were kindly provided by T. Mitchell (University of Glasgow) and were grown in Todd-Hewitt broth (Acumedia) with 2% yeast extract. After overnight incubation at 37° C. and 5% $CO_2$, we re-inoculated bacteria into fresh media, cultured them to mid-logarithmic growth phase ($A_{600}=0.4$), centrifuged them at 1,500 g for 5 min, washed them once and resuspended them in PBS. We performed infections as follows unless otherwise stated. We infected mice weighing 18-20 g with a dose of $2\times10^5$ colony-forming units (CFU) of bacteria in 100 µl by i.p. injection. At 24-h intervals after injection, we collected blood to enumerate bacterial CFU in circulation and to measure hematologic parameters as we monitored the time to death. Unless otherwise indicated, those mice with equivalent bacteremia (between $1\times10^4$ CFU/ml and $1\times10^6$ CFU/ml at 24 h after infection followed by an increase to between $1\times10^6$ CFU/ml and $1\times10^8$ CFU/ml at 48 h after infection) were studied further. For platelet half-life determination, we injected mice with biotin 1 h before *S. pneumoniae* infection.

We generated the *S. pneumoniae* NanA$^T$ strain (expressing neuraminidase in trans) from the isogenic *S. pneumoniae* D39 NanA mutant strain transformed with a PDC123 plasmid containing the *S. pneumoniae* nanA gene. An overnight culture of *S. pneumoniae* grown in brain heart infusion medium (Fluka) was re-inoculated into fresh media with 1 mM $CaCl_2$. When the cultures had reached $A_{600}=0.1$, we added competent stimulate peptide-1 (CSP-1) to a final concentration of 100 ng/ml before further incubation at 37° C. for 15 min. We added 100 ng plasmid PDC123 containing the nanA gene to this culture before plating it on a chloramphenicol-selective Todd-Hewitt broth plus 2% yeast extract (Becton Dickinson) plate for growth at 37° C. with 5% $CO_2$ overnight for positive colony selection.

Statistical analyses. All data are presented as the means±s.e.m. unless otherwise indicated. We analyzed numeric data for statistical significance using Student's unpaired t-test with Prism software (GraphPad). We considered P values of less than 0.05 as statistically significant. Degrees of statistical significance are presented as *P<0.001, P<0.01 or *P<0.05.

Results
Ashwell Receptors Govern vWF Homeostasis

We observed localization of the vWF glycoprotein in situ primarily among liver endothelial cells, but also among hepatocytes; in which the majority of vWF colocalized with the Asgr-1 chain of the Ashwell receptor (FIG. 1*a*). In contrast, there was markedly less colocalization of hepatocyte vWF with Asgr-2 (FIG. 1*b*). In mice homozygous for null mutations in either Asgr1 or Asgr2 (Ishibashi, S. et al., *J. Biol. Chem.*, 269:27803-27806 (1994); Soukharev, S. et al., *Nucleic Acids Res.*, 27:e21 (1999)), the other closely linked gene retained function, and the corresponding Asgr glycoprotein remained expressed (FIG. 1c). Furthermore, the absence of Asgr-1, but not of Asgr-2, reduced the total amount of vWF associated with hepatocytes, resulting in an increased percentage of the remaining vWF that colocalized with Asgr-2 (FIG. 1c).

Circulating plasma vWF abundance was increased 1.5-fold in mice lacking Asgr-1 in comparison either to mice lacking Asgr-2 or wild-type (WT) littermates (FIG. 1d). The elevated vWF in Asgr-1 deficiency was paralleled by an increased abundance of plasma factor VIII, a procoagulation factor that binds to and is stabilized by vWF in the circulation (FIG. 1e). No changes in vWF or factor VIII were observed in Asgr-2-deficient mice, and factor IX, factor XI and factor XII were unaffected in mice with null mutations in either Asgr1 or Asgr2 (FIG. 1e). Elevated abundance of plasma vWF in Asgr-1-deficient mice correlated with increased vWF half-life in the circulation (FIG. 1f). Nonetheless, the elevation of vWF levels did not result in an increase in the frequency of asialo-vWF (data not shown). These findings reveal that the Ashwell receptor is normally engaged in the control of endogenous vWF clearance and homeostasis, implying a receptor-ligand relationship and suggesting a role in modulating blood coagulation and thrombosis.

Functional Intersection of the Ashwell Receptor and ST3Gal-IV

Mice lacking Asgr-1 had a reduced bleeding time compared to WT littermates, whereas their counterparts lacking Asgr-2 were unaffected (FIG. 1g). Because ASGPR-mediated clearance of vWF occurs in ST3Gal-IV sialyltransferase deficiency, we hypothesized that the Ashwell receptor and ST3Gal-IV may jointly control endogenous vWF homeostasis. We studied mice bred to lack ST3Gal-IV function as well either Asgr-1 or Asgr-2. Asialo-vWF was detected by the absence of sialic acid linkages at the termini of various glycan chains using plant-derived galactose binding lectins as previously described (Ellies, L. G. et al., *Proc. Natl. Acad. Sci. USA*, 99:10042-10047 (2002)) and was the dominant vWF glycoform in circulation in all strains of mice lacking ST3Gal-IV function (data not shown). Notably, the diminished abundance and shortened half-life of plasma vWF due to ST3Gal-IV deficiency were restored to normal by the additional loss of Asgr-1, whereas, in contrast, loss of Asgr-2 did not result in such a rescue (FIG. 1h and data not shown). Moreover, Asgr-1 deficiency also corrected the prolonged bleeding and activated partial thromboplastin times in the absence of ST3Gal-IV, which is consistent with normalization of circulating vWF and consequently factor VIII abundance (FIG. 1h and data not shown).

Unexpectedly, mice lacking Asgr-2 and ST3Gal-IV, despite their vWF deficit, had a marked reduction in bleeding time compared to mice lacking only ST3Gal-IV (FIG. 1h). Because platelets that are deficient in sialic acid linkages (asialo-platelets) are also found in the circulation of mice lacking ST3Gal-IV function, with resultant thrombocytopenia (low platelet count) due to ASGPR-mediated clearance (Ellies, L. G. et al., *Proc. Natl. Acad. Sci. USA*, 99:10042-10047 (2002)), we suspected that the Ashwell receptor might also control platelet homeostasis.

The Ashwell Receptor in Platelet Homeostasis

Circulating platelet counts were unaffected in mice homozygous for either Asgr1 or Asgr2 mutation; however, the low platelet counts of mice with ST3Gal-IV deficiency were restored to normal in littermates that further lacked either Asgr-1 or Asgr-2 (FIG. 2a). Platelet volume, reticulated (newly formed) platelet abundance, and platelet half-life were also normalized (FIG. 2b-d). No alterations in red blood cell half-life occurred in parallel measurements (data not shown).

The liver is a major anatomic site of normal platelet clearance, and Kupffer cells, the resident macrophages of the liver, contribute to this clearance activity (Stratton, J. R. et al., *J. Nucl. Med.*, 30:629-637 (1989); Hoffmeister, K. M. et al., *Cell*, 112:87-97 (2003)). Hepatocytes are not generally considered to have a significant role. However, platelets have been observed within hepatocytes in some contexts, and the ability of hepatocytes to clear desialylated platelets has been recently reported in studies of platelet binding and internalization (Nakamura, M. et al., *J. Hepatol.*, 28:991-999 (1998); Rumjantseva, V. et al., *Blood* (ASH Annual Meeting Abstracts), 108:1523 (2006)). We observed that the majority of platelets in the livers of WT mice are normally associated with Kupffer cells (FIG. 2e). In ST3Gal-IV-deficient mice, despite an overall increase in platelet sequestration in the liver, there was a decrease in the percentage of platelets associated with Kupffer cells (FIG. 2e). In the acute setting of plasma transfusion, biotinylated asialo-platelets derived from ST3Gal-IV-deficient donors were more abundant in the livers of post-transfused wild-type recipients, and the majority were associated with hepatocytes, as compared to the abundance and localization of post-transfused biotinylated WT platelets bearing normal abundance of sialic acid linkages (FIG. 2f). We conclude that ST3Gal-IV deficiency exposes endogenous glycan ligands on platelets that are recognized by the Ashwell receptor in an inter-action that promotes asialo-platelet clearance by hepatocytes and leads to thrombocytopenia.

Bacterial Sialidase Activity and the Ashwell Receptor

The location, high capacity and rapid kinetics of ligand clearance by the Ashwell receptor is consistent with its anticipation of a sudden and widespread alteration of endogenous glycoprotein structure within the circulatory system. Such conditions might arise after infection by pathogens that encode sialidase (neuraminidase) activity, such as *Streptococcus pneumoniae*, a leading cause of sepsis and the life-threatening thrombohemorrhagic disorder known as disseminated intravascular coagulation, manifested by rapid consumption of platelets and coagulation factors (Camara, M. et al., *Infect. Immun.*, 62:3688-3695 (1994); Bryant, A. E., *Clin. Microbiol. Rev.*, 16:451-462 (2003); Franchini, M. et al., *Thromb. J.*, 4:4 (2006)).

We administered a lethal dose of *S. pneumoniae* (isolate D39) to WT mice by intraperitoneal (i.p.) injection and monitored platelet glycosylation in mice with comparable bacterial counts in the blood before death. Circulating platelets were progressively desialylated during *S. pneumoniae* sepsis, as evidenced by an increase in galactose exposure (FIG. 3a). In contrast, loss of sialic acid from the surface of red blood cells was not detected. Infection of WT mice with an isogenic nanA mutant strain of *S. pneumoniae* lacking the sialidase enzyme NanA (Winter, A. J. et al., *Infect. Immun.*, 65:4411-4418 (1997)) (NanA$^-$) did not generate asialo-platelets in circulation (FIG. 3b). Bacteremia during the progression of sepsis after infection of WT mice with the *S. pneumoniae* NanA$^-$ isogenic mutant was similar to that seen with infection by the parental *S. pneumoniae* D39 strain (*S. pneumoniae* WT), in contrast to a previous finding in which an *S. pneumoniae* NanA$^-$ isolate failed to propagate in circulation 38. Complementation of NanA activity in trans (NanA$^T$) restored platelet desialylation similar to that seen with *S. pneumoniae* WT (FIG. 3c). These studies identify the bacterial NanA neuraminidase as the sialidase responsible in sepsis for platelet desialylation.

The thrombocytopenia that occurs in sepsis is believed to reflect accelerated platelet consumption due to increased blood coagulation. Upon infection of WT mice with *S. pneumoniae* WT, thrombocytopenia developed before death, as expected (FIG. 3d). In contrast, when the same challenge was applied to Asgr-1-deficient mice, platelet levels were comparable to those in uninfected mice (FIG. 3d). Normal platelet counts were also present in WT mice infected with the *S. pneumoniae* NanA⁻ mutant, whereas thrombocytopenia was again triggered when the *S. pneumoniae* NanA⁻ mutant was complemented with the intact nanA gene (FIG. 3d). Consistent with these findings, platelet half-life decreased during *S. pneumoniae* WT infection of WT mice but was unaltered in mice lacking Asgr-1 after an identical challenge (FIG. 3e). The Ashwell receptor is not itself involved in controlling sialidase function, as the amount of platelet desialylation produced by *S. pneumoniae* NanA was identical in WT and Asgr-deficient hosts (data not shown). In addition, vWF was desialylated during *S. pneumoniae* WT infection at higher bacterial loads, and under these conditions there was evidence of increased clearance of asialo-vWF (FIG. 3f). Thus, during *S. pneumoniae* sepsis, the hepatic Ashwell receptor is responsible for the induction of thrombocytopenia in response to platelet desialylation by the bacterial NanA sialidase.

The Ashwell Receptor Reduces Coagulopathy and Increases Survival

Figure 4:
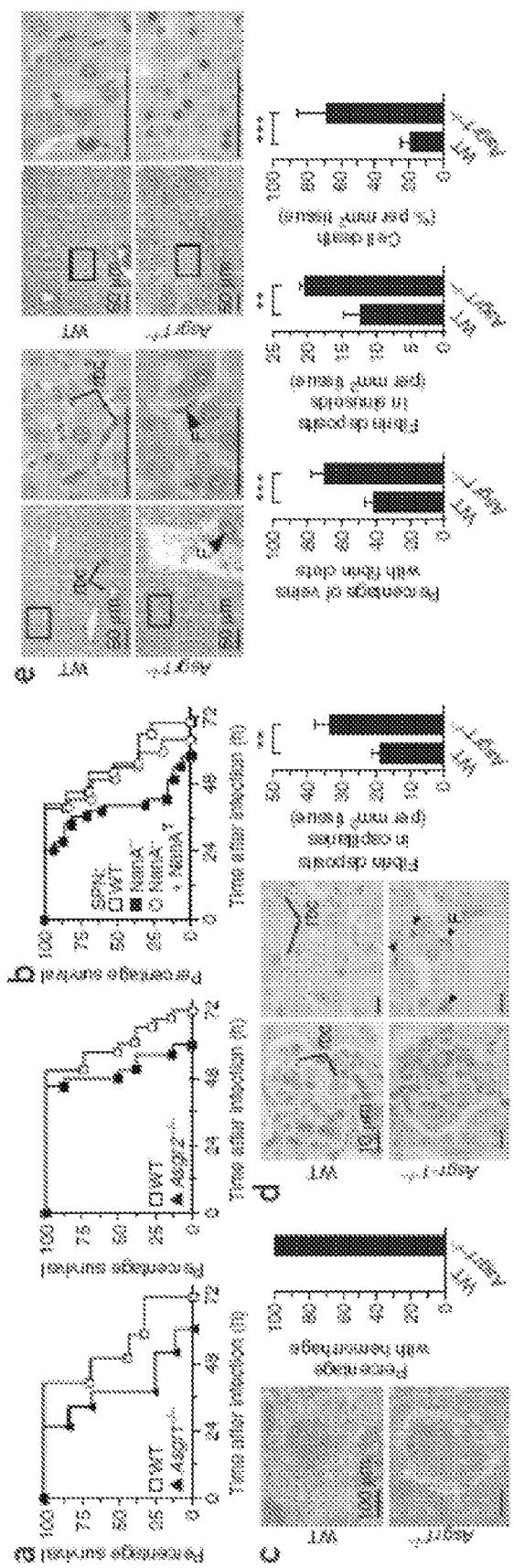
FIG. 4 Extension of lifespan and reduction in coagulopathy by the Ashwell receptor in lethal *S. pneumoniae* infection. (a) Survival times of WT and Asgr-deficient mice after infection with a lethal dose of *S. pneumoniae* WT. (b) Survival times of WT mice infected with *S. pneumoniae* variants that retain or lack NanA sialidase activity. (c-e) Tissue histopathology in mice of the indicated genotypes 24 h after infection with *S. pneumoniae* WT. (c) Hemorrhage of the spleen with involvement of the lymphoid follicles occurred in all mice lacking Asgr-1. Data are representative of results from eight littermate pairs. (d) In the kidney, reduced vascular flow and increased deposition of fibrin (F) were evident in capillaries of the glomeruli and between the tubules. Rbc, red blood cell. (e) In the left four images, fibrin deposition was also markedly increased in the veins and sinusoids of the liver in Asgr-1 deficiency (left and center graphs). In the right four images, hepatocyte death was detected by the presence of pyknotic nuclei (right graph). Boxed regions are shown enlarged to the right. Scale bars denote 100 µm (c), 10 µm (d) and 50 µm (e). Images in c-e are representative of 20-30 randomly selected fields of view used for quantitation. These studies included six or more littermate comparisons of the indicated genotypes infected with equivalent doses of *S. pneumoniae* variants ($2 \times 10^5$ CFU administered i.p.). All comparisons were performed on mice with equivalent levels of bacteremia. *$P < 0.001$ and $P < 0.01$. All values are means±s.e.m.
Figure 5:
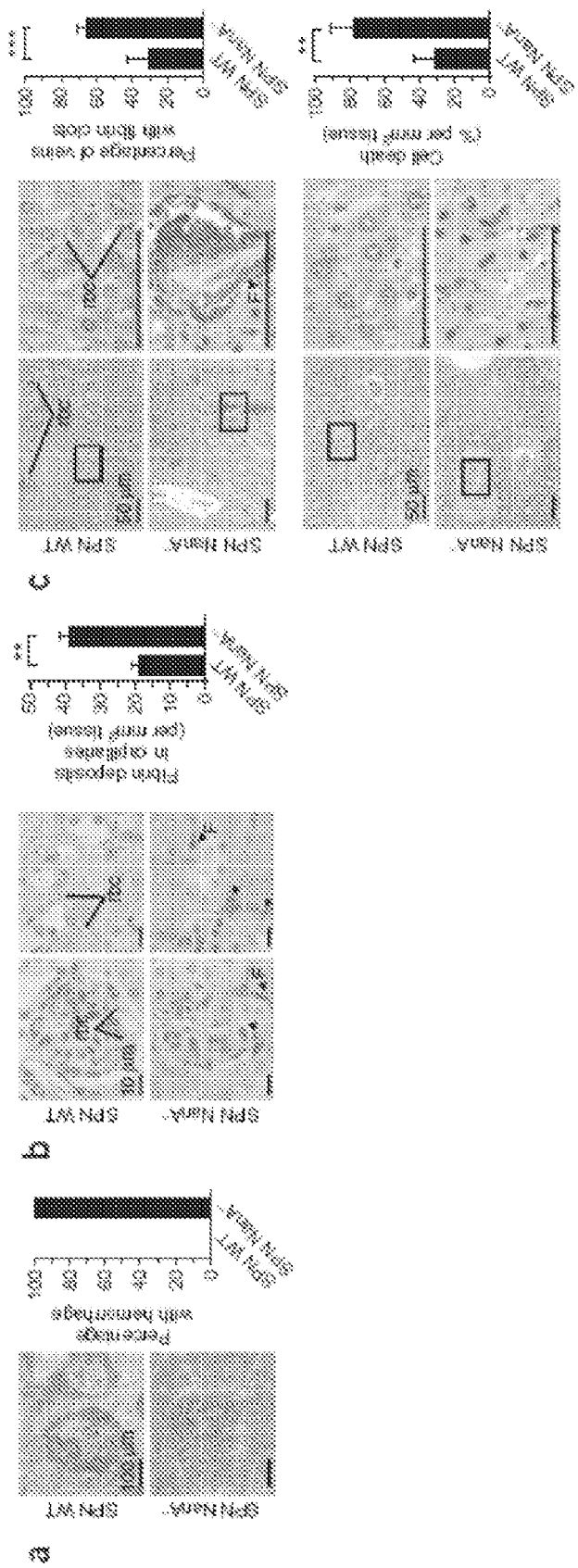
FIG. 5 Increased severity of coagulopathy in sepsis after infection with the *S. pneumoniae* NanA⁻ mutant. Tissue histopathology in WT mice 24 h after infection with *S. pneumoniae* WT (D39) or *S. pneumoniae* NanA⁻. (a) Splenic hemorrhage occurred in all mice infected with the *S. pneumoniae* NanA⁻ strain. (b) Accumulation of fibrin (F, arrowheads) and impaired vascular flow are evident among capillaries of kidney glomeruli and between tubules. (c) Fibrin deposition in liver veins and pyknotic nuclei indicating cell death. Boxed regions are shown enlarged to the right. Scale bars denote 100 µm (a), 10 µm (b) and 50 µm (c). Images are representative of 18-24 randomly selected fields of view used to quantify results. These studies include three to six littermate comparisons of the indicated genotypes infected with equivalent doses of *S. pneumoniae* variants ($2 \times 10^5$ CFU administered i.p.). All comparisons were performed on mice with equivalent levels of bacteremia. *$P < 0.001$ and $P < 0.01$. All values plotted are means±s.e.m.
Figure 6:
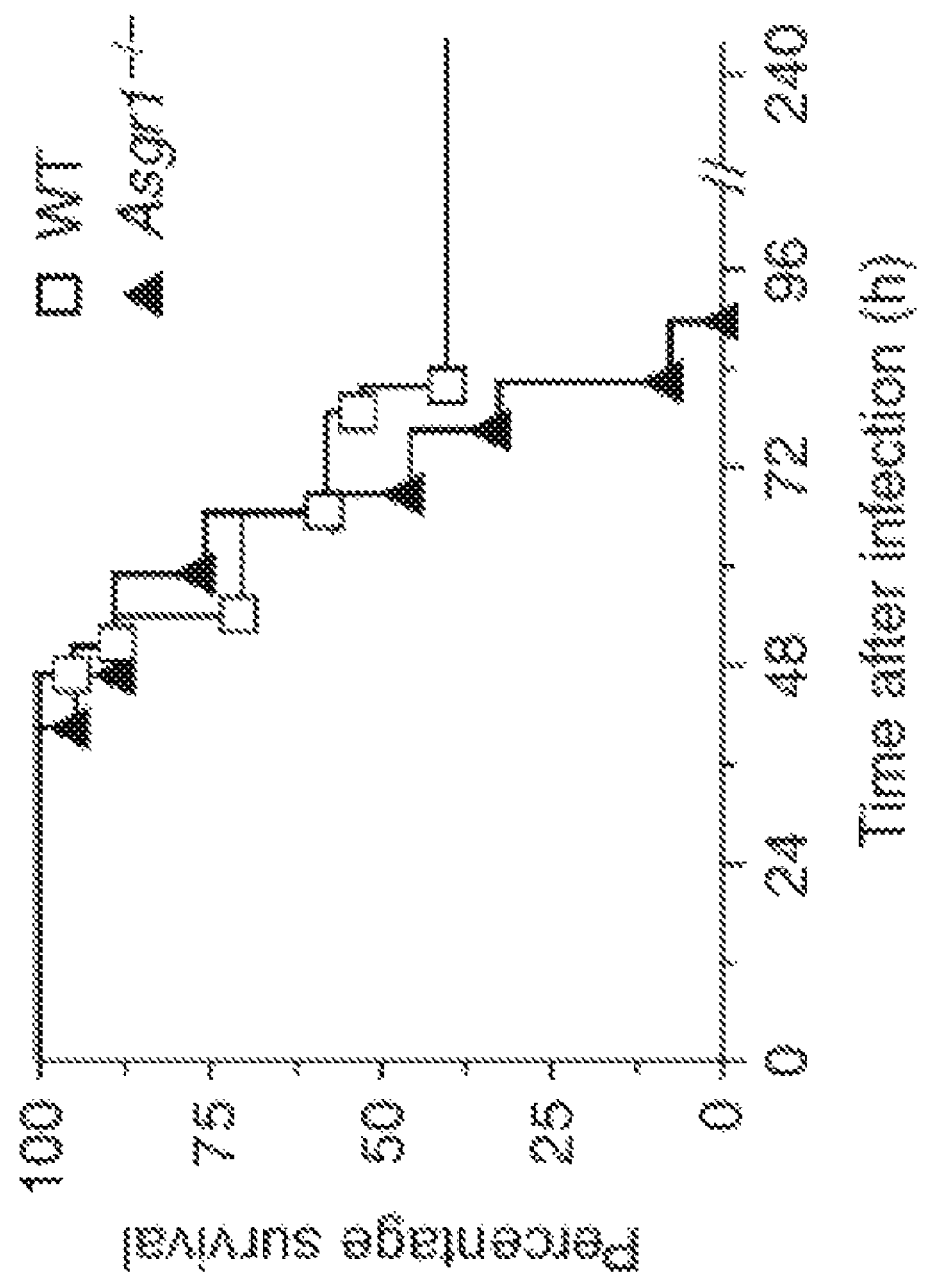
FIG. 6 The Ashwell receptor decreases mortality in *S. pneumoniae* sepsis. None of the 15 Asgr-1-deficient mice survived infection with a low dose of *S. pneumoniae* WT (D39) ($1 \times 10^3$ CFU administered i.p.). In contrast, 6 of 16 WT littermates survived. This finding was reproduced in three independent experiments with additional cohorts of mice.

We suspected that the reduction of prothrombotic factors during *S. pneumoniae* sepsis might moderate the pathologic outcome in the host. Thus, we determined the time to death after *S. pneumoniae* WT infection. Mice retaining Ashwell receptor function survived considerably longer than littermates that were deficient in either Asgr-1 or Asgr-2; whereas those lacking Asgr-1 succumbed most rapidly (FIG. 4a). Of note, WT mice rendered septic by the *S. pneumoniae* NanA⁻ mutant also died sooner than those infected with *S. pneumoniae* WT, mirroring the decreased survival time associated with Asgr-1 deficiency, whereas complementation of the NanA⁻ mutant restored survival times to similar values as observed with *S. pneumoniae* WT infection (FIG. 4b). We suspected that Ashwell receptor function may moderate the severity of disseminated intravascular coagulation during sepsis. When mice had comparable bacteremia, and on average 12 h before their expected time of death, we undertook histopathological analysis of organs and tissues. Hemorrhage of the spleen was observed in all mice lacking Asgr-1 but was absent from WT littermates (FIG. 4c). In addition, vascular occlusion and fibrin deposition were markedly elevated in the kidney in the absence of Asgr-1 (FIG. 4d). Further signs of severe disseminated intravascular coagulation were observed in the liver of Asgr-1-deficient mice, with increased fibrin deposition in sinusoids and more severe venous thromboembolic occlusion (FIG. 4e). These pathological findings in Asgr-1-deficient mice were coincident with an increase in hepatocyte cell death (FIG. 4e). A similar increase in the severity of disseminated intravascular coagulation, including fibrin deposition, thrombosis and hemorrhage portending multi-organ failure, was also observed in WT mice rendered septic by the *S. pneumoniae* NanA⁻ mutant (FIG. 5). Notably, in a lower-dose challenge model using *S. pneumoniae* WT, all Asgr-1-deficient mice succumbed to infection, compared to a 37% survival rate of WT hosts (FIG. 6). The Ashwell receptor thus impedes the pathogenesis of disseminated intravascular coagulation and improves the probability of host survival in *S. pneumoniae* sepsis.

Example 2

This example shows that treatment with either an antibody specific to a platelet antigen (anti-CD41 mAb) or neuraminidase reduces circulating platelet levels by enhancing their clearance from blood. In particular, these treatments provide a decreased time to death and survival advantage during severe sepsis.

Methods

Infection and Treatment of Mice

The experimental C57BL/6 mice were obtained at 12-14 weeks of age from Harlan (Indianapolis, Ind.) and groups of 10-14 mice were infected with $3 \times 10^3$ *S. pneumoniae* WT by intraperitoneal injection. Either 20 μg anti-CD41 mAb (Clone MwReg30, BD Biosciences) or anti-rat IgG control (eBiosciences) or 0.4 U Neuraminidase diluted in 100 μl PBS was administered into the lateral tail-vein or the retro-orbital venous sinus at 20-40 hrs post *S. pneumoniae* infection, when bacteremia was evident. No difference was observed between these routes of delivery. At times of treatment or sham delivery, levels of bacteria in the blood were determined to be at a minimum counts of $1 \times 10^2$ CFU/ml as described (Grewal et al., 2008 *Nat. Med.* 14:648-55). No significant difference in bacteremia or survival was observed between *S. pneumoniae* infected mice treated with either IgG or PBS. Neuraminidase treatments used sialidase enzymes from *Arthrobacter ureafaciens* (EY Labs, CA, SEQ ID NO: 2) or *Vibrio cholerae* (SEQ ID NO: 4) with equivalent results; data are pooled. De-sialylation of circulating platelets was confirmed by flow cytometry analyses of blood collected at time intervals and stained with ECA and RCA lectins as described (Grewal et al., 2008); platelets were de-sialylated at 1 hr following neuraminidase delivery.

Statistical Analyses

Survival data was plotted as Kaplan-Meier survival curves to obtain median survival times. The number (n) of mice analyzed and percent survival are provided. The survival times were compared with Log-rank test with p values as indicated. Statistical significance was determined as $p < 0.05$. GraphPad Prism 4.0 software was used in the analyses.

Results

Figure 7:
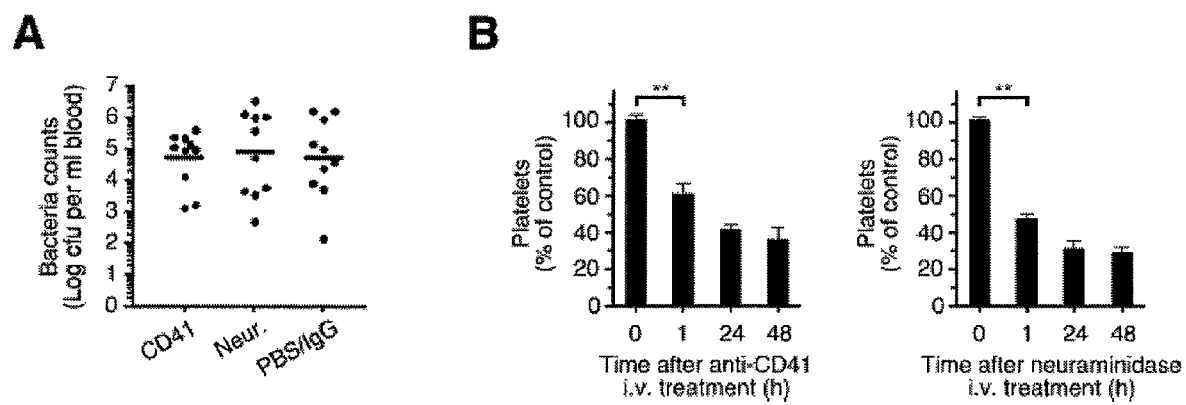
FIG. 7 (a) Bacteremia levels in blood following intraperitoneal infection with $3 \times 10^3$ CFU. Levels of bacteremia detected in the blood at 24 hours following SPN infection ranged from $10^2$ to $10^7$ CFU/ml. There was no significant difference in the mean bacteria counts between the experimental groups prior to administration of anti-CD41 or neuraminidase treatment or PBS/IgG. (b) Reduction in circulating platelets levels was observed in mice 1-24 h following anti-CD41 or neuraminidase i.v. administration, **$p < 0.01$. Data plotted as means+/−s.e.m.
Figure 8:
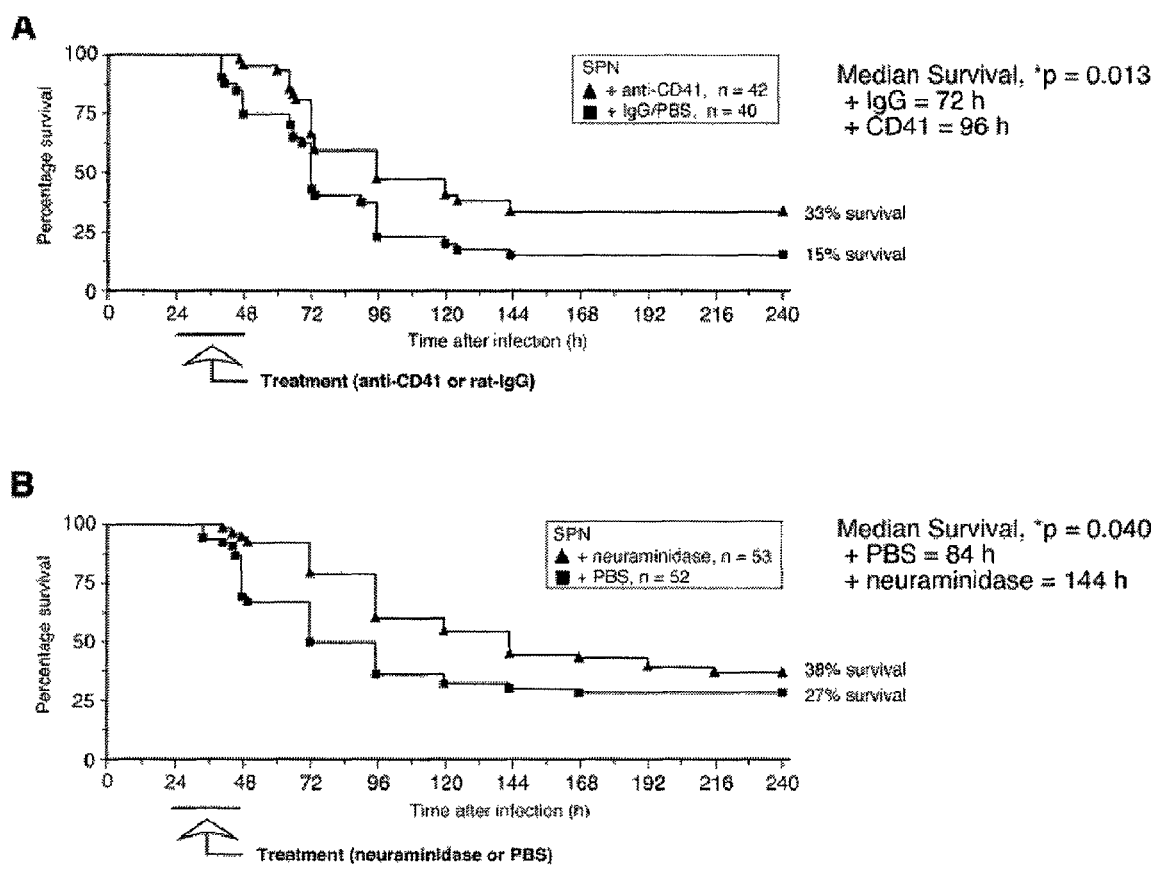
FIG. 8 (a) Mice treated early during SPN infection with either anti-CD41 mAb or (b) neuraminidase are provided with an increased survival time. Median survival times are significantly increased in the treatment groups compared to controls (rat IgG or PBS treated), *$p < 0.05$. An increase in cumulative survival rate is also observed as indicated by % survivors within each group.

Groups of 10-14 mice injected intraperitoneally with wild type strain D39 *Streptococcus pneumoniae* (SPN) to induce sepsis. At 24 h following infection, when bacteria could be detected in the blood, mice were provided with single therapeutic treatments of anti-CD41 or neuraminidase to promote reduction in circulating platelet levels. Reduction in circulating platelets levels was observed in mice 1-24 h following anti-CD41 or neuraminidase i.v. administration (FIG. 7). There was a significant increase in median survival times between anti-CD41 or neuraminidase treated mice and controls (IgG or PBS treated) (*$p < 0.05$). An increase in the total percentage of survivors was also observed for both treatment groups (FIG. 8).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating coagulopathy in a patient, the method comprising administering to the patient a therapeutically effective amount of a neuraminidase polypeptide that increases clearance of coagulation factors or platelets.

2. The method of claim 1, wherein the coagulopathy is associated with infection by a pathogen.

3. The method of claim 2, wherein the pathogen lacks neuraminidase activity.

4. The method of claim 2, wherein the pathogen has neuraminidase activity.

5. The method of claim 2, wherein the pathogen is a bacterium.

6. The method of claim 5, wherein the bacterium is *Streptococcus pneumoniae*.

7. The method of claim 1, wherein the coagulopathy is associated with carcinoma, massive tissue injury, snake bite, heat stroke, or liver disease.

8. The method of claim 1, wherein the coagulopathy is disseminated intravascular coagulation (DIC).

9. The method of claim 1, wherein the neuraminidase is a bacterial neuraminidase.

10. The method of claim 9, wherein the neuraminidase is from *Arthrobacter ureafaciens*.

11. The method of claim 9, wherein the neuraminidase is from *Vibrio cholerae*.

12. The method of claim 1, further comprising administering to the patient a sialyltransferase inhibitor.

13. The method of claim 12, wherein the sialyltransferase inhibitor inhibits the sialyltransferase ST3Gal IV.

14. The method of claim 12, wherein the sialyltransferase inhibitor is an analog of a sialyltransferase.

* * * * *